(12) United States Patent
Pologe

(10) Patent No.: US 6,647,279 B2
(45) Date of Patent: Nov. 11, 2003

(54) HYBRID OPTICAL DELIVERY SYSTEM FOR PHOTOPLETHYSMOGRAPHY

(76) Inventor: Jonas Alexander Pologe, 515 Hartford Dr., Boulder, CO (US) 80305-5714

( * ) Notice: Subject to any disclaimer, the term of this patent is extended or adjusted under 35 U.S.C. 154(b) by 1 day.

(21) Appl. No.: 10/104,316

(22) Filed: Mar. 22, 2002

(65) Prior Publication Data

US 2003/0181796 A1 Sep. 25, 2003

(51) Int. Cl.[7] .................................................. A61B 5/00
(52) U.S. Cl. ........................ 600/322; 600/323; 600/344
(58) Field of Search ................................ 600/322, 323, 600/340, 344

(56) References Cited

U.S. PATENT DOCUMENTS 5,891,022 A   4/1999  Pologe
6,253,097 B1 * 6/2001 Aronow et al. ............. 600/323

* cited by examiner

Primary Examiner—Eric F. Winakur
Assistant Examiner—David J. McCrosky

(57) ABSTRACT

A hybrid optical system for photoplethysmographic measurements is disclosed. The system delivers light from a plurality of emitters to the tissue-under-test. A set of one or more of the emitters resides in close proximity to the sensor. A second set of one or more emitters resides at some distance from the sensor with the light from this second set of emitters being delivered to the sensor by a light pipe typically consisting of a fiber optic cable. This invention allows the photoplethysmographic instrument designer to use two or more different types of emitters in the same photoplethysmographic device while still generating a technically feasible and cost effective design.

22 Claims, 2 Drawing Sheets

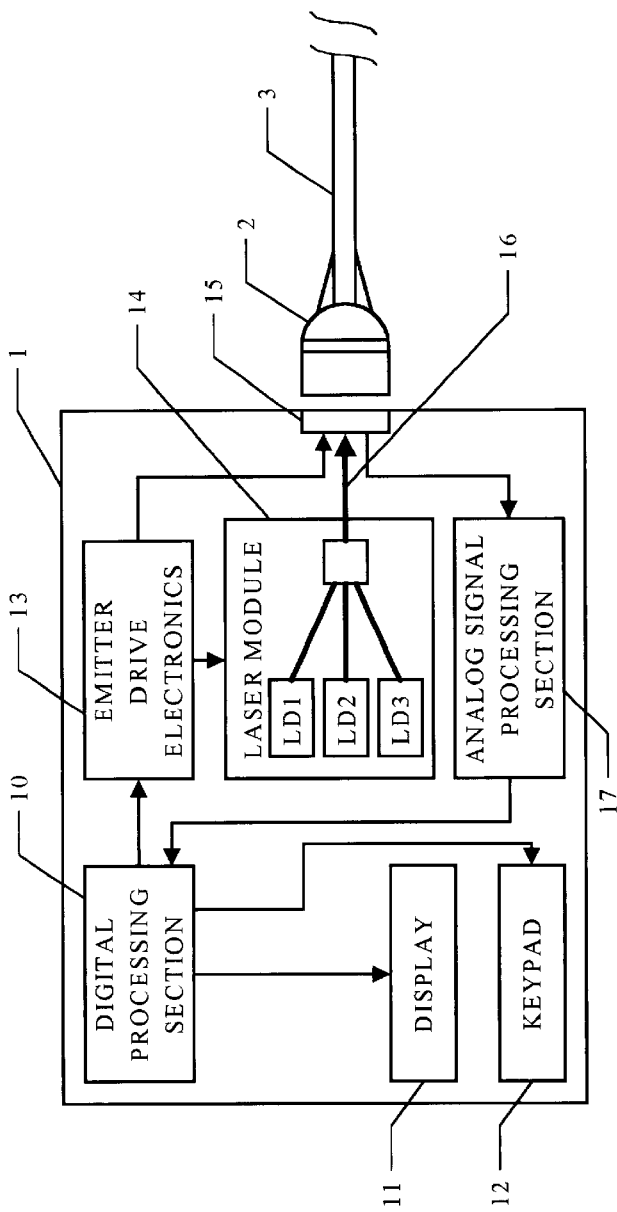
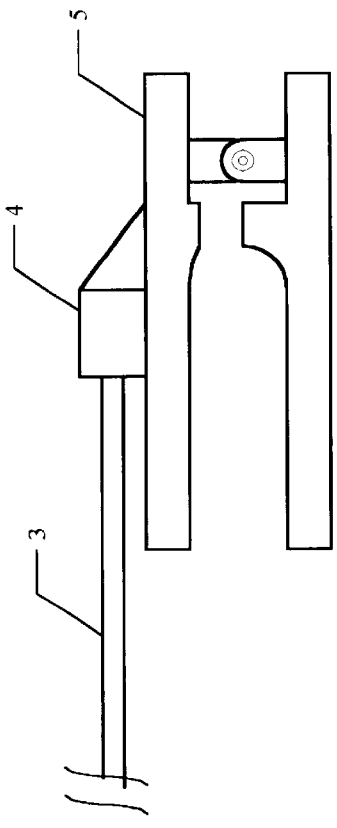
FIG. 1
FIG. 2

HYBRID OPTICAL DELIVERY SYSTEM FOR PHOTOPLETHYSMOGRAPHY

FIELD OF THE INVENTION

The present invention relates in general to systems for performing photoplethysmographic measurements of various blood analytes and other hemodynamic parameters.

BACKGROUND OF THE INVENTION

In the science of photoplethysmography, light is used to illuminate or trans-illuminate tissue for the purpose of measuring blood analytes or other hemodynamic or tissue properties. In this monitoring modality, light is injected into living tissue and the light which is not absorbed by the tissues is detected a short distance from the entry point. The detected light is converted into an electronic signal, indicative of the received light signal from the tissue. This electronic signal is then used to calculate one or more physiologic parameters such as arterial blood oxygen saturation, heart rate, cardiac output, or tissue perfusion. Other blood analytes that may be measured by photoplethysmography include the percentages of oxyhemoglobin, carboxyhemoglobin, methemoglobin, and reduced hemoglobin in the arterial blood.

The first commercial use of photoplethysmography in medicine was in the pulse oximeter, a device designed to measure arterial blood oxygen saturation. Since the inception of this device, this monitoring modality has been used to detect more and more different parameters. For example, a device has recently been disclosed which is capable of measuring the percentages of four different analytes in the arterial blood, including oxyhemoglobin, carboxyhemoglobin, methemoglobin and reduced hemoglobin. To make these measurements a number of different bands of light must be used, with each light band possessing a unique spectral content. Each spectral band is usually referred to by the center wavelength, or sometimes by the peak wavelength, for the given band. In the case of pulse oximetry for instance, two different light emitting diodes (LEDs) are typically used to generate the sensing light, the first with a center or peak wavelength around 660 nanometers (nm) and a second with a center or peak wavelength around 940 nm.

As the number of different parameters measured by photoplethysmography increases, so too does the number of different bands of light required to make the measurements. Further, because a fairly high intensity of light, over a fairly narrow spectral range is needed for these measurements, it has been found that the most successful sources of light for these measurements have been discrete, narrow-band emitters such as LEDs or laser diodes. These types of light sources are typically used because broadband sources have too little energy over the desired narrow spectral ranges to provide sufficient signal amplitude for photoplethysmographic measurements.

As the number of light sources, or emitters, used in a single device increases, the problems associated with how to deliver the light to the tissue-under-test also increases. These problems are created by several different factors. These include the ergonomic constraints placed on photoplethysmographic instrumentation by the medical community, cost constraints, reliability concerns, emitter operating parameters, and technical feasibility considerations. In the design of a multi-parameter photoplethysmographic device, it is desirable to use a selection of emitters with the best optical properties possible for the analyte measurements of interest and in an opto-mechanical configuration that best meets the technical, ergonomic, and cost constraints of the instrument.

BRIEF SUMMARY OF THE INVENTION

In the science of photoplethysmography, light is used to illuminate, or trans-illuminate, tissue for the purpose of measuring blood analytes or hemodynamic properties or parameters. In making these measurements it can become necessary to use light from a number of different sources including but not limited to LEDs, incandescent bulbs, or lasers.

Each of these different sources has different properties that dictate how the light will be delivered to the tissue under test. For example, use of LEDs allows the light source to be placed in the sensor and directly proximate to the tissue-under-test. Additionally, it is difficult to couple LED light into a secondary light-delivering apparatus such as a fiber optic cable, making it technically difficult to position the LEDs at a distance from the sensor. Note that for the purposes of this document the 'sensor' is defined as that portion of the system that is placed directly on the tissue-under-test.

By comparison, laser light sources (particularly currently-available conventional semiconductor lasers) require thermal stabilization to maintain a proper spectral output and, when mounted with their necessary thermal controllers and heat sinks, are too bulky to be placed directly on the sensor. Instead the laser or lasers are preferably placed in the instrument or in a housing at some intermediate point on the patient cable. The laser light can be transmitted to the sensor via some type of light pipe, typically a fiber optic cable of some type. Laser light sources are also typically more expensive and considerably more fragile than LEDs, which are additional reasons to place these types of components at a distance from the sensor and in a housing that can adequately protect them.

Incandescent light sources are also difficult to position at the sensor. They tend to be large, hot, and require a certain amount of optics to make them useful for photoplethysmographic devices. Again, these properties make it desirable to place any incandescent sources some distance from the sensor.

With the increasing complexity of photoplethysmographic devices detecting and measuring more and more parameters, it becomes necessary to design systems with large numbers of emitters. In an effort to maximize measurement accuracy, it can be beneficial to utilize a multitude of emitters of different types. For example in the specific instrument of this invention, one capable of monitoring four different species of hemoglobin and the heart rate, it is desirable to use three or more laser diodes and one or two LEDs. This allows for the measurement system to utilize the different optical properties of the different emitters in the same system. For the specific instrument described herein, the optical stability of the LEDs' output light is required for measurement of low perfusion patients, and the extremely narrow-band output of the laser diodes makes possible the measurement of optical absorption of a hemoglobin species on very steep portions of its extinction curve.

A hybrid optical system, containing multiple emitters of more than one type, makes photoplethysmographic measurements possible that are otherwise not feasible or which could otherwise not be made to clinically acceptable levels of accuracy and precision.

One aspect of this invention therefore is the use of multiple types of emitters in the same photoplethysmographic system. A second aspect of this invention is the optimal placement of the different emitters, with some type or types typically positioned at the sensor and other types positioned in an intermediate housing or inside the instrument housing, to create the most optimal configuration both mechanically and optically while maximizing reliability and minimizing product cost.

This emitter layout creates a problem for the instrument designer in that the lasers are difficult to position at the sensor and the LEDs are difficult to position at a distance from the sensor. In past designs of photoplethysmographic devices, the emitters were all of one type and were all positioned either at the sensor with their output light directly incident on the tissue-under-test or the emitters were all positioned at a distance from the sensor and the light piped to the sensor by a light guide. This invention allows the photoplethysmographic instrument designer to utilize the beneficial optical properties of multiple and different types of emitters in the same design while permitting the positioning of these emitters at different locations in the photoplethysmographic system for optimal coupling of the output light into the tissue-under-test.

A further aspect of this invention is the co-location of the output light from the various sources to cause the light from all emitters to be incident on the same small area of the tissue-under-test, thus forcing the output light from all the light sources to follow the same optical path. This is a necessary condition for accurate photoplethysmographic measurements in tissue.

BRIEF DESCRIPTION OF THE DRAWINGS

FIG. 1 is a block diagram of the photoplethysmographic instrument showing the control flow, front panel connector, cable connector, and sensor cable.

FIG. 2 is a sketch of the sensor cable, sensor connector, and a durable finger sensor used in conjunction with the photoplethysmographic instrument.

DETAILED DESCRIPTION OF THE INVENTION

Figure 3:
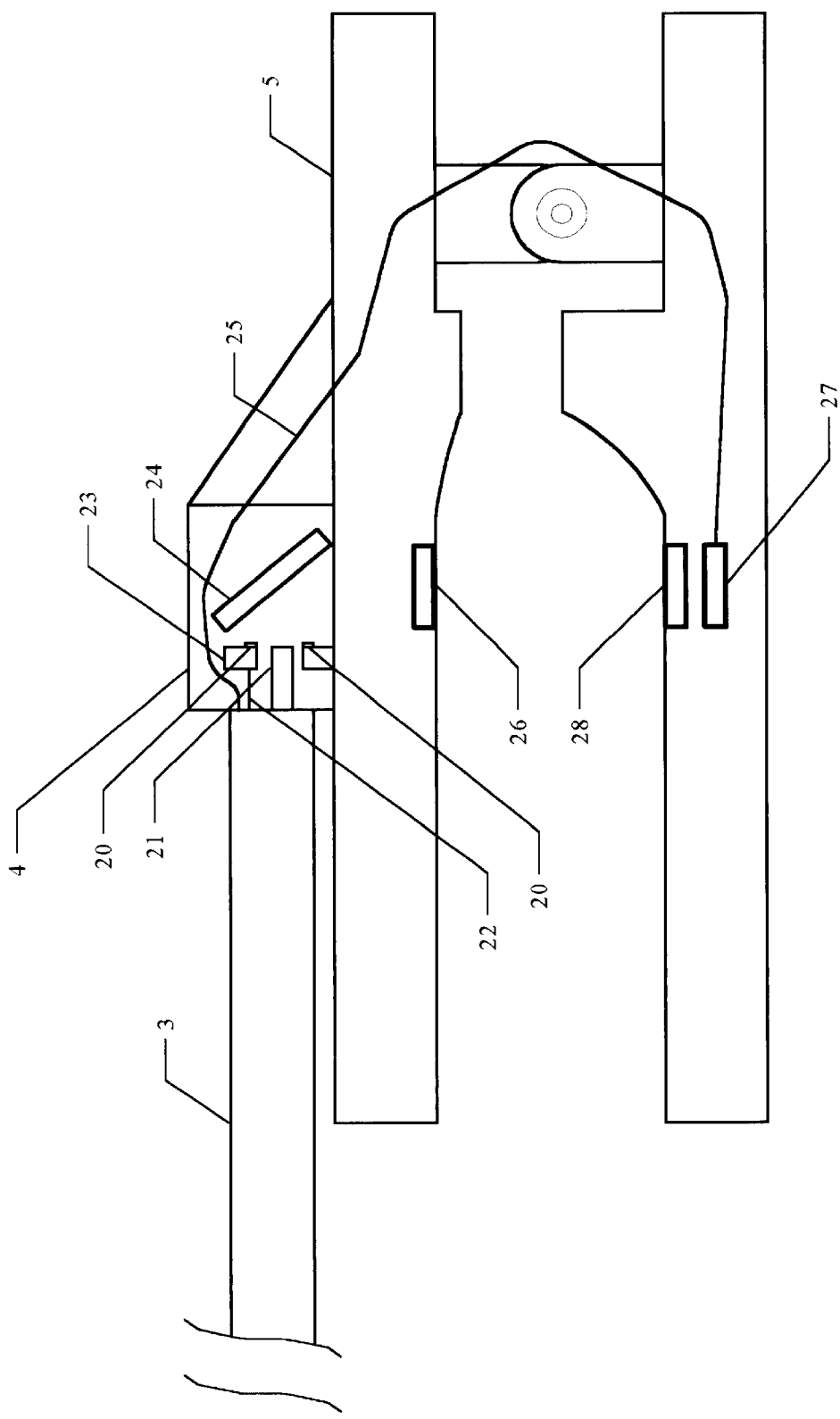
FIG. 3 is a detailed drawing of the sensor connector, and sensor.

Prior to this device all photoplethysmographic devices have housed the emitters, or sources, for the system at the same physical location. They have also used only one type of emitter in any given system. Thus if we examine an early photoplethysmographic device, the Minolta/Marquest Oxygen Saturation Monitor, Model SM-32, we see that a single incandescent light source was used. The output light from this lamp was transmitted by fiber optics to the tissue-under-test. The light that was not absorbed or scattered by the tissues was then collected and carried back to the instrument via a second fiber bundle. Note that the light collected was limited to the light that exited the tissue at the contact point for the second fiber bundle. This light was then transmitted back to the instrument where it was filtered through two interference filters to create two separate bands of light each with a distinct spectral content. It was the analysis of these two different bands of light that allowed the photoplethysmographic measurements.

Unfortunately, filtering broadband sources of light into narrowband sources, for use in the photoplethysmographic measurements eliminates the majority of the light intensity and barely leaves a usable quantity of light. As a result the Minolta/Marquest Oxygen Saturation Monitor had a great deal of difficulty functioning on a broad range of patients with a broad range of optical densities. An improvement over this design was the next generation of pulse oximeters that utilized LEDs to generate the different bands of light necessary for the photoplethysmographic measurements. The first of these devices, the BIOX II, was made by Bioximetry Technology, Inc. and used two LEDs installed in the sensor. The LEDs generated light centered at approximately 660 nm and 940 nm with much greater intensities then was possible with the earlier incandescent system. Since BIOX II all commercially available pulse oximeters have used LED sources, typically housed in the sensor itself. Some photoplethysmographic systems have been made that position the sources at a distance from the sensor and use fiber optics to pipe the light to the tissue-under-test. While these LED-based systems utilizing fiber optics to transmit and receive the light have been shown to work, they suffer from extremely low signal levels and are generally only used in devices designed to work in a magnetic resonance imaging (MRI) environment without interfering with the MRI readings.

More recently in a patent by Pologe, J A (U.S. Pat. No. 5,891,022), a device was revealed that utilizes two or more emitters, typically laser diodes, where the output light is coupled into individual fibers and then coupled into a single fiber or fiber bundle to then be carried to the tissue-under-test. The emitters and their accompanying thermal control and heat sinking elements were housed at a distance from the sensor. In this device, once again, all light sources were housed in the same location.

The present invention relates to a system for performing photoplethysmographic measurement utilizing multiple types of emitters positioned at multiple locations, both proximal to and at a distance from the tissue-under-test. This configuration allows for optimizing the optical properties of the selected emitters, maximizing the light intensities incident on the tissue-under-test, maximizing system reliability, and minimizing system noise.

In one embodiment, as illustrated in FIGS. 1 through 3, both light emitting diodes (LEDs) and laser diodes are used in the same instrument. In FIG. 1 the Photoplethysmographic Instrument 1 is shown. The arrows in this figure show the control and signal flow in the instrument. The Digital Processing Section 10 controls all operations in the instrument, calculates the measured analyte levels and the other physiological parameters, and runs the user interface accepting input from the Keypad 12 and displaying the measured parameters on the instrument Display 11. In alternate embodiments, output might also be provided to other interfaces such as a digital interface for connection to an external computer system or in analog form for connection to such analog devices as an external strip chart recorder. The Digital Processing Section 10 also controls the Emitter Drive Electronics 13. Most photoplethysmographic systems are run in a time division multiplexed manner with the emitters turned on one at a time in a repetitive cycle. This allows a single Photodiode 27, shown in FIG. 3, to receive light from all the different emitters and for the instrument to be able to discern from which emitter the light is being received at any given point in time. Unique to this invention, the Emitter Drive Electronics 13 (FIG. 1) control the timing of two different sets of emitters, each set positioned in a physically different location. The first set of emitters is housed in the Photoplethysmographic Instrument 1 and a second set is housed in the Sensor 5. In the preferred embodiment, the emitters housed in the instrument are contained in the Laser Module 14. This module contains a set of laser diodes that are coupled into a fiber, a fiber bundle, or some other type of light guide 16, for transmission to the sensor and on to the tissue-under-test. A second set of emitters is housed in the Sensor 5 and the Emitter Drive Electronics 13 provides control signals for these emitters as well.

It should be noted that this embodiment shows the first set of emitters housed within the Photoplethysmographic Instrument 1. It is also possible to house this set of emitters in a separate housing positioned between the Photoplethysmographic Instrument 1 and the Sensor 5. This would not change the intent of this invention, as the output light from this set of emitters would still need to be conducted or piped to the sensor through some sort of light guide.

Finally, the light from the Laser Module 14 and the emitter drive signals, for the LEDs, from the Emitter Drive Electronics 13 are passed to the Front Panel Connector 15 to interface with the Patient Cable 3. The Patient Cable 3 connects to the Photoplethysmographic Instrument 1 by way of the Patient Cable Connector 2, which plugs directly into the Photoplethysmographic Instrument 1. Returning from the Sensor 5 is an electronic signal representative of the received light intensities picked up by the Photo-Detector 27 in the Sensor 5. This signal is passed on to the Analog Signal Processing Section 17.

The Analog Signal Processing Section 17 along with the Digital Processing Section 10, process (processing refers to filtering, amplification, analog-to-digital conversion, and mathematical calculations performed on the signal.) the signal received from the Sensor 5 to measure and calculate the parameters of interest.

In FIG. 2 a Sensor 5 is shown which is used to attach the photoplethysmographic system to the tissue-under-test. This figure shows a sketch typical of the type of durable Sensor 5 that might be used for connection to a patient's finger. The Sensor 5 is connected to the Patient Cable 3 by means of the Sensor Connector 4. In the current embodiment, the Patient Cable 3 and the Sensor Connector 4 are a fixed unit that is detachable from the Sensor 5. In this way, alternate sensor types may be attached to same patient cable. It is not uncommon for manufacturers of photoplethysmographic devices to have five or more different types of sensors for attachment in different ways and to different parts of the body as well as a variety of sensor sizes for use on patients ranging from neonates to adults.

FIG. 3 shows, in detail, the current embodiment for the Patient Cable 3, Sensor Connector 4, and the Sensor 5. The signal controlling the second set of emitters, originating in the emitter drive electronics, enters the printed circuit board (PCB) 23 by way of the Drive Cable 22. These are the electronic signals that, in this embodiment, drive the LEDs 20 housed on the PCB 23. These LEDs make up the second set of emitters that are housed directly at the sensor. The light from these emitters can be directly incident on the Output Aperture 26, or, as in this embodiment, reflected off the Mirror 24 used to direct all light from all emitters toward the output aperture.

The PCB 23, shown in cross section in FIG. 3. In the current embodiment, it is designed as a small circular PCB that positions the LEDs radially around the Light Guide 21 which protrudes through the center of the PCB. The goal of this particular design is to create a small and homogeneous set of light sources that, from the point of view of the output aperture, appear to be a single point source as required for photoplethysmographic measurements.

In this invention two sets of emitters are used. One is located at the Sensor 5 and a second set is located in the Photoplethysmographic Instrument 1. A design of this type allows the use of different types of emitters in the same instrument. The Photoplethysmographic Instrument 1 houses the laser diodes, whereas the LEDs are housed at the Sensor 5. Laser diodes are expensive and have a considerably shorter lifetime then LEDs, therefore it is important to minimize the number of laser diodes utilized in a given design. It can also be beneficial to house the lasers inside the instrument housing to allow for additional physical protection of these components and to provide the space needed for heat sinks or cooling devices such as fans or thermoelectric coolers. Because lasers have a very narrow bandpass they are necessary for the measurement of certain analytes where the broader bandpass of other emitter types such as LEDs would not allow sufficient accuracy of measurement or may make the desired measurement impossible to attain.

LEDs can be used when extremely short bandpass is not required for measurement accuracy. They also have the advantages of being extremely durable, very inexpensive, and extremely stable in their output light levels. Unfortunately LEDs have a very wide spatial irradiance pattern and are not physically small enough to behave like a point source when being coupled into optical fibers. Due to these properties it is difficult to obtain high efficiency coupling from LEDs into optical fibers. Since the intensity of the light incident on the tissue-under-test is directly proportional the signal-to-noise ratio it is optimal to allow the LEDs to shine directly onto the output aperture to avoid the losses in intensity associated with fiber optic coupling. Thus this invention combines the two modalities for supplying light to the tissue-under-test allowing multiple types of emitters to be used in the same photoplethysmographic system. This provides the benefits derived from each type of emitter enhancing the number of analytes that can be measured and the accuracy with which they can be measured.

It is important in photoplethysmographic systems that the light incident on the tissue-under-test enters the tissue from the same aperture regardless of which emitter generated the light. The optical and geometric configuration of the Sensor 5 and the Sensor Connector 4 therefore must be designed such that this condition is met. In the embodiment shown in FIG. 3, the Mirror 24 reflects the light generated remotely, i.e. by the emitter set housed in the photoplethysmographic instrument and transmitted to the sensor via the Light Guide 21, and locally, i.e. by the local set of LED emitters, and reflects these signals towards the Output Aperture 26. The light guide in this embodiment consists of a set of optical fibers each coupled to one of the remote emitters. The type of light guide used can be individual optical fibers, either glass or plastic, a fiber bundle, or even a liquid light guide. It is only important that the type of light guide used has properties that make it functional in a medical instrument. In general the light guide should be as thin and flexible as possible and minimize the losses to the light it is transmitting. It is also possible to couple more than one emitter into any given light guide so that there is not necessarily a one to one correspondence between the number of remote emitters and the number of light guides used. The Mirror 24 also allows for the light output from the light guide and the LEDs to spread out, fully filling the output aperture, and therefore co-locating the light from all sources. With this design, the criterion that all light sources enter the tissue-under-test through the same aperture is met. This is necessary to ensure that the path the light takes through the tissue-under-test to the Detector Aperture 28 is essentially identical for all emitters.

The light that exits the tissue via the Detector Aperture 28 is incident upon the Photo-detector 27, where it is converted to an electronic signal representative of the incident light. In the preferred embodiment of this device, the photo-detector of choice is a silicon-based photodiode. This device type is utilized because it is an inexpensive device that has a very low noise level, making it ideal for the low-level signals received by the photo-detector in typical photoplethysmographic devices. These low-level signals consist of two primary components of the light transmitted by the tissue-under-test, after attenuation by the targeted blood analytes, other light absorbers, and scattering elements in the tissue. These two signal components are a DC, or constant signal, component and an AC, or a time-varying signal, component. The time-varying component is that portion of the light signal that fluctuates up and down in amplitude as the blood volume in the tissue-under-test pulsates down and up, i.e. out of phase, with each heartbeat. It is this AC component that can be extremely small in amplitude, sometimes less than 0.1% of the DC component. Both the AC and DC components must be accurately measured many times a second to allow for accurate photoplethysmographic measurement of the targeted parameters. These components of the received light signal, or their electronic equivalents, can be measured independently or as single, combined amplitude. Thus it is this electronic signal, representative of the light incident on the Photo-detector 27, that is transmitted back to the Photoplethysmographic Instrument 1, via the Detector Cable 25, for processing.

The previous discussion of the invention has been presented for the purposes of illustration and description. The description is not intended to limit the invention to the form disclosed herein. Variations and modifications commensurate with the above are considered to be within the scope of the present invention. The embodiment described herein is further intended to explain the best mode presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

What is claimed is:

1. A photoplethysmographic measurement apparatus for measuring one or more blood analyte levels or one or more hemodynamic parameters in a tissue-under-test, comprising:
   a plurality of separate emitters, wherein each emitter produces a light signal having a unique spectral content, said emitters separated into two sets of at least one emitter each;
   a sensor which makes direct contact with the tissue-under-test and provides an output aperture through which light signals are delivered to the tissue-under-test;
   housing means for housing each of the two sets of emitters in two separate locations, said housing means comprising a first housing means located proximal to said sensor and a second housing means located some distance from said first housing means;
   means for transporting said light signals from said first and said second housing means to said sensor;
   means for guiding the light signals from said first and second housing means through said output aperture to be incident on the tissue-under-test;
   means for receiving a portion of the light signal exiting the tissue-under-test and converting said received light-signal to an electronic signal indicative of the said received light signal;
   means for processing said received light signal to determine one or more blood analyte levels or one or more hemodynamic parameters.

2. The apparatus as claimed in claim 1 wherein said sensor provides the opto-mechanical means to co-locate all of the said output light signals to pass through said output aperture to be incident upon the tissue-under-test.

3. The apparatus as claimed in claim 2 wherein said first housing means resides in said sensor immediately proximal to the tissue-under-test.

4. The apparatus as claimed in claim 2 wherein said first housing means is located inside a connector that is removably attached to said sensor.

5. The apparatus as claimed in claim 3 wherein said first housing means is permanently attached to said sensor.

6. The apparatus as claimed in claim 2 wherein said two sets of emitters are of distinctly different types of optical sources.

7. The apparatus as claimed in claim 6 wherein at least one set of said emitters consists of a plurality of one or more light emitting diodes.

8. The apparatus as claimed in claim 6 wherein at least one set of said emitters consists of a plurality of one or more laser diodes.

9. The apparatus as claimed in claim 2 wherein said means for transporting said light signals from said emitters in said second said housing means to said sensor includes one or more of the following group comprising, optical fibers, an optical fiber bundle, plastic fiber, and a single liquid core guide.

10. The apparatus as claimed in claim 2 wherein said blood analyte levels consists of the measurements of the percentages of oxyhemoglobin, carboxyhemoglobin, methemoglobin and reduced hemoglobin in the arterial blood.

11. A photoplethysmographic measurement apparatus for measuring the concentrations of a plurality of blood analytes, in a tissue-under-test, comprising:
    a plurality of light emitters, said emitters separated into two sets of at least one emitter each;
    a sensor which makes direct contact with the tissue-under-test and provides an output aperture through which light signals are delivered to the tissue-under-test;
    a photo-detector which receives a portion of the remaining light signal output from the tissue-under-test and converts said light signal to an electronic signal indicative of said light signal incident on the photo-detector;
    a processing means which converts said electronic signal into blood analyte levels wherein said blood analytes includes at least two of the group comprising: oxyhemoglobin, carboxyhemoglobin, methemoglobin, reduced hemoglobin, and reduced hemoglobin;
    an output means that generates a user readable output of said blood analyte levels;
    housing means for housing each of the said two sets of emitters in two separate locations, said housing means comprising a first housing means located proximal to said sensor and a second housing means located some distance from said sensor;
    means for transporting said light signals from said second said housing means to said sensor;
    means for guiding all of said light signals through said output aperture.

12. An apparatus as claimed in claim 11 wherein each emitter produces a light signal having a unique spectral content.

13. In a photoplethysmographic measurement system, a method for measuring one or more blood analyte levels or one or more hemodynamic parameters in a tissue-under-test, said method comprising the steps of:

providing a plurality of separate emitters, wherein each emitter produces a light signal having a unique spectral content, said emitters separated into two sets of at least one emitter each;

providing a sensor which makes direct contact with the tissue-under-test and providing an output aperture through which light signals are delivered to the tissue-under-test;

providing a housing means for housing each of the two sets of emitters in two separate locations, said housing means comprising a first housing means located proximal to said sensor and a second housing means located some distance from said first housing means;

providing a means for transporting said light signals from said first and said second housing means to said sensor;

guiding the light signals from said first and second housing means through said output aperture to be incident on the tissue-under-test;

providing a means for receiving a portion of the light signal exiting the tissue-under-test and converting said received light signal to an electronic signal indicative of the said received light signal;

processing said received light signal to determine one or more blood analyte levels or one or more hemodynamic parameters.

14. The method of claim 13 further comprising the step of:
substantially co-locating all of said output light signals to pass through said output aperture to be incident upon the tissue-under-test.

15. The method of claim 14 further comprising the step of:
positioning said first housing means to reside in the sensor immediately proximal to the tissue-under-test.

16. The method of claim 14 further comprising the step of:
positioning said first housing means inside a connector that is removably attached to said sensor.

17. The method of claim 15 further comprising the step of:
positioning said first housing means permanently attached to said sensor.

18. The method of claim 14 further comprising the step of:
including said two sets of emitters wherein the said sets contain emitters consisting of distinctly different types of optical sources.

19. The method of claim 18 further comprising the step of:
including a plurality of one or more light emitting diodes in at least one set of said emitters.

20. The method of claim 18 further comprising the step of:
including a plurality of one or more laser diodes in at least one set of said emitters.

21. The method of claim 14 further comprising the step of:
transporting said light signals from said emitters in said second said housing means to said sensor using one or more of the following group comprising, optical fibers, an optical fiber bundle, plastic fiber, and a single liquid core guide.

22. The method of claim 14 further comprising the step of:
measuring said blood analyte levels including the measurements of the percentages of oxyhemoglobin, carboxyhemoglobin, methemoglobin and reduced hemoglobin in the arterial blood.

* * * * *